(12) United States Patent
Li et al.

(10) Patent No.: US 7,453,916 B2  
(45) Date of Patent: Nov. 18, 2008

(54) HIGH THROUGHPUT OPTICAL MICRO-ARRAY READER CAPABLE OF VARIABLE PITCH AND SPOT SIZE ARRAY PROCESSING FOR GENOMICS AND PROTEOMICS

(75) Inventors: Ruolin Li, Santa Clara, CA (US); Guoying Ding, Sunnyvale, CA (US)

(73) Assignee: Intel Corporation, Santa Clara, CA (US)

( * ) Notice: Subject to any disclaimer, the term of this patent is extended or adjusted under 35 U.S.C. 154(b) by 465 days.

(21) Appl. No.: 11/222,992

(22) Filed: Sep. 8, 2005

(65) Prior Publication Data

US 2007/0054280 A1    Mar. 8, 2007

(51) Int. Cl.  
*H01S 5/00* (2006.01)

(52) U.S. Cl. ............................ 372/50.12; 372/50.124
(58) Field of Classification Search ........... 372/50.12, 372/50.124
See application file for complete search history.

(56) References Cited

U.S. PATENT DOCUMENTS

2004/0061042 A1*  4/2004  Almogy et al. ........ 250/208.1

* cited by examiner

*Primary Examiner*—Dung T Nguyen  
(74) *Attorney, Agent, or Firm*—Darby & Darby PC

(57) ABSTRACT

An optical micro-array reader system includes microchip, VCSEL, microlens and detector arrays. The microchip array includes multiple sample spots to be separately analyzed. The VCSEL array is disposed to simultaneously illuminate more than one of the multiple spots. The microlens array focuses fluorescences or other optical emissions from the sample spots onto the detector array.

32 Claims, 2 Drawing Sheets

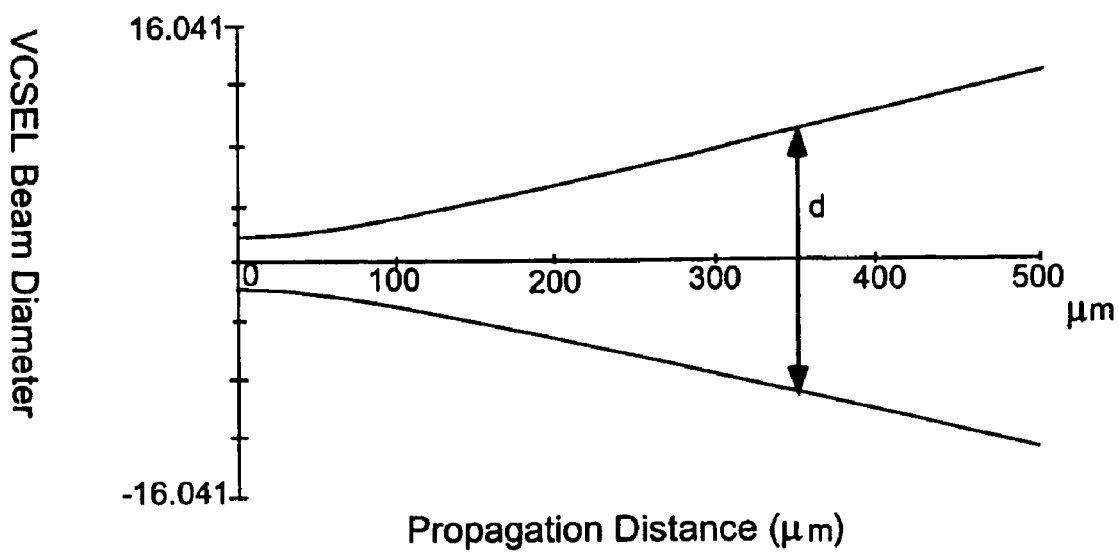
Figure 3
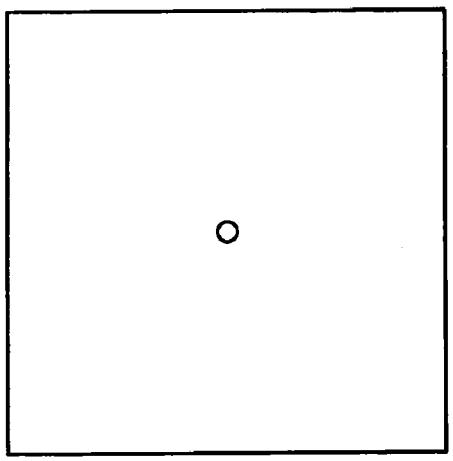 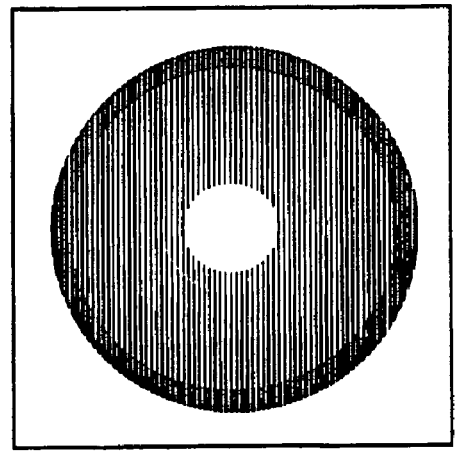
Figure 4A          Figure 4B

HIGH THROUGHPUT OPTICAL MICRO-ARRAY READER CAPABLE OF VARIABLE PITCH AND SPOT SIZE ARRAY PROCESSING FOR GENOMICS AND PROTEOMICS

BACKGROUND

1. Field of the Invention

The invention relates to and/or alternatively utilizes bio-chip processes, DNA research, drug discovery, genomics, and proteomics, vertical cavity surface emitting lasers (VCSELs), microarrays, fluorescence studies, array pitches and spot sizes, variable beam focus, and array reading.

2. Description of the Related Art

DNA microarrays have emerged as powerful tools applicable to numerous high-throughput screening assays such as genotyping, gene expression analysis, gene mutation detection, DNA sequencing, and ELISA immunoassays. DNA microarray-based assays offer tremendous potential in both diagnostic and pharmaceutical applications due to their extreme versatility and miniaturized formats. Specifically, functional applications such as population-wide genetic screening, clinical diagnostics, and disease risk analysis and drug toxicity are advantageously suited for microarray formats due to small sample volume requirements, multiplexed parallel configurations, and susceptibility to customization.

In today's microarray analysis technology, there are thousands to a half million spots on a single micro-array chip. Most current technology processes the spot in a scanning manner, i.e., only one spot at a time is measured. This method is time consuming and inefficient. It is desired to have a higher throughput spot analysis process to solve a great bottleneck for DNA, protein, and cell research.

Conventional optical sensor array equipment uses discrete external light sources. For detection and quantification of highly miniaturized and multiplexed microarray assays, achieving both enhanced throughput and cost reduction for demanding medical applications will involve utilizing laser-based screening techniques. Vertical Cavity Surface Emitting Lasers (VCSELS) are attractive light sources that may be integrated with optical sensor array equipment because of their low cost, well-collimated beam profile, narrow spectral bandwidth, and low power consumption. With tremendous technology development on VCSELs recently triggered by telecommunication, visible VCSELs are also becoming available. The application of VCSELs to bioanalysis will greatly benefit and enhance developments in geno-research.

BRIEF DESCRIPTION OF THE DRAWINGS

FIG. 3 is a plot that illustrates how the diameter of a divergent Gaussian VCSEL beam increases with propagation distance.

FIGS. 4A and 4B illustrate beam profiles of a VCSEL laser (8 μm waist) at 0 and 1 mm travel distance, with the Gaussian beam diameters being 8 and 60 μm at these two locations, respectively.

DETAILED DESCRIPTION OF THE PREFERRED EMBODIMENTS

Figure 1:
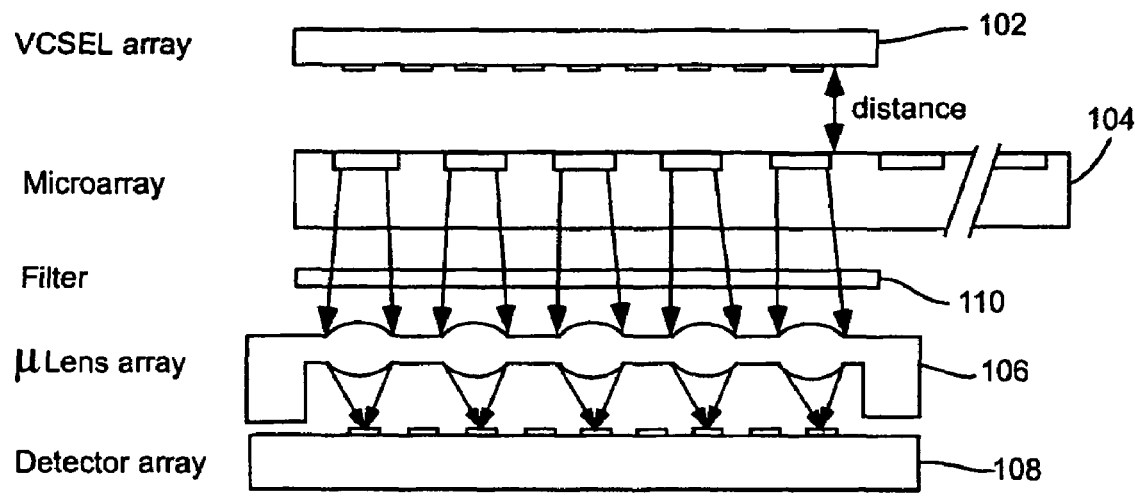
FIG. 1 illustrates an optical reader configured to simultaneously probe multiple spots of a microarray in accordance with a preferred embodiment.

An optical microarray sensor system or optical reader in accordance with a preferred embodiment is illustrated at FIG. 1. The system includes a VCSEL array light source 102, microarray chip 104, focusing optical micro-lens array 106, and a detector array 108. A laser line filter 110 is also shown in FIG. 1 disposed between the microarray chip 104 and the detector array 108.

It is preferred to utilize VCSELs at least having a wavelength around ~850 nm. Any of a wide variety of VCSEL types may be used as distinguished based on emission wavelengths and manufacturing processing. The choice will depend upon the micro-array material and what wavelength will cause it to flouresce, and typical micro-array materials have their best absorption in the visible/near-IR.

The VCSEL array 102 illuminates part or all of an m×n microarray to excite fluorescence for gene analysis or other biotechnological study. At least two microarray sample spots are illuminated simultaneously.

The VCSEL array 102 may be a linear array. During a fluorescence measurement process, the linear array may be stepped from row to row or column to column until all of the sample spots of the microarray 104 have been illuminated and measured. The VCSEL array may also be a 2D VCSEL array capable of illuminating multiple rows and multiple columns simultaneously. Alternatively, a certain row or column may be selectively energized depending upon optical or geometric characteristics of the light spot or spots desired at a particular time. As described in a further embodiment below, some VCSELs may be offset in a direction perpendicular to the array in order that the distances between certain subsets of VCSELs in the array and the micro-array differ. In this embodiment, the VCSEL array 102 may be considered to be a 3D array.

The VCSEL array 102 may be an i×j subarray of the larger m×n microarray 104. The I×j microarray is stepped i rows at a time. When the end of the columns is reached, j columns are skipped and the system steps down the columns again I rows at a time. The process may continue likewise until all of the columns are stepped through, and all of the sample spots have been illuminated and measured.

The VCSEL array 102 may also include an m×n array. In this embodiment, the fluorescences of the sample spots of the entire m×n microarray 104 may be measured simultaneously.

Less than all of the VCSELs may be fired at the same time. There are various reasons and research scenarios that make this feature advantageous. For example, the microarray 104 or the filled sample spaces of the microarray 104 may not be rectangular, such that there may be some columns or rows that include more samples to illuminate than others. By firing only the VCSELs that correspond to sample spots to be illuminated, energy is saved and noise is reduced.

In another feature of the system that will be described in more detail below, some sample spaces in the microarray 104 may be larger than others. A minimum sample area may be determined by a minimum level of detectable flourescence or absorption, and so will be dependent upon the sample. It is typically possible to get a spot size on the order of 2 um or larger. To efficiently illuminate samples having various spot sizes, some VCSELs may be spaced at greater fixed or adjustable distances from the microarray 104 than others, or the VCSEL carriage may include VCSELs that are relatively spaced at different distances from the plane of the microarray 104. Then, VCSELs spaced further from the microarray 104 may be selected when it is desired to increase the illumination spot size to match a larger sample size. In another advantageous alternative embodiment, the VCSELs 102 or the microarray 104, or both, may be moveable to adjust the distance between the VCSELs 102 and the microarray 104.

Other reasons may exist wherein the ability to selectively energize VCSELs may be used. For example, some VCSELs may generate different wavelengths, bandwidths, energies, or cross-sectional intensity profiles than others, and so certain VCSELs may be selected for better illumination of particular samples than others.

The 2D micro-lens array 106 is preferably used to focus the fluorescence from the sensing spots of the microarray 104 onto the detector array 108. Mirrors may be used instead of lenses 106. The lenses 106 are made from a material that has high transmission around the fluorescence wavelengths of interest. There may be lenses in the microlens array 106 made of different materials responsive to different fluorescence wavelengths of same or different samples. There may be different size lenses or optical powers corresponding to different sample sizes, different desired illumination spot sizes, distances to the detector, and/or detector spot size. The lenses may be a same size large enough to accommodate the largest anticipated spot size and/or some lenses may be disposed at a different distance from the microarray 104 so that different spot sizes at the plane of the microarray 104 can be accommodated by same lens sizes disposed in different planes, and/or some lenses of the microlens array 106 may have different diameters than others.

Fluorescence spectral data are collected by the detector array 108, and interface electronics and processing bio-analysis software may be used to process and store the spectral data. The detector array 108 (and/or the lens array 106) may also be adjustable in case the focal plane changes with adjustments that may be made with the VCSEL array 102 and microarray 104 to accommodate different sample sizes.

Preferably, the detectors 108 are "standard" pin photodetectors which absorb in the region of interest. Visible light can be detected with AlGaAs based pins, and IR light with InGaAsP pins. Resonant cavity pin detectors may also be used because they have a spectral filtering characteristic which can be helpful when it is desired to reject the VCSEL light signal. Additionally Avalanche Photodetectors (APDs) may be used to provide optical gain to the signal, which can be helpful when the emitted signal is very small and amplification is desired.

The filter 110 may be used to reject the excitation light so that preferably the intensity distribution of the light that reaches the detector array 108 includes primarily the fluorescence signal emitted by a sample at the microarray chip 104. This permits the sensitivity of the detector 108 to be set optimally based on the intensity of the fluorescence signal, and reduces the noise level so that the fluorescence signal may be more easily resolved. There are alternatives to using an absorption filter 110 such as setting the propagation direction of the light at an angle such that the laser light substantially misses to the detector 108 to one side, or utilizing an optic that transmits the laser line and reflects the fluorescence or an optic that reflects the laser line and reflects the fluorescence, or utilizing a detector that is insensitive at the laser line yet is sensitive at the fluorescence line. The preferred absorption filter and each of these alternatives, along with other ways to permit the fluorescence light to be measured and included in the research results, serve to permit the fluorescence light to be detected and measured, while substantially excluding the laser light from influencing the results preferably by keeping the laser light from being incident at the detector 108. Electronic filtering using electronics and/or software may also be used alternatively or in addition to optical or mechanical filtering.

The device may be alternatively configured to operate reflectively. In this case, the VCSELs and detectors would be on the same plane or at least on the same side of the plane of the micro-array. The light would preferably reflect from the substrate at an angle to feedback into the detector.

The invention is not limited to flourescence detection. Other detection such as absorbance detection may be monitored by, e.g., configuring the detector array to be sensitive to the correct wavelength band. Detection of emitted Raman spectra is also possible with sufficiently high input laser power. Even if the VCSELs utilized for fluorescence measurements are insufficient, other laser sources may be used (e.g., diode, YAG or other solid state lasers, or gas lasers such as $CO_2$, noble gas ion, or excimer lasers). Methods may be used to boost the laser power or focus the beam down to a smaller spot to increase the energy density.

Figure 2:
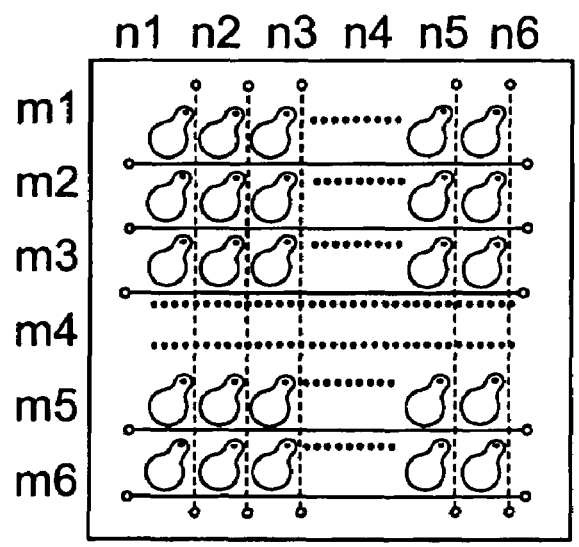
FIG. 2 illustrates a M×N VCSEL array in accordance with a preferred embodiment that is designed and fabricated in such a way that rows and/or columns can be turned on and off selectively.

FIG. 2 illustrates a m×n VCSEL array in accordance with a preferred embodiment that is designed and fabricated in such a way that rows and/or columns can be turned on and off selectively. As shown, there are six rows m1 through m6 and six columns n1 through n6. In the example of FIG. 2, the VCSELS of row m4 and those of column n4 are each turned off, while the rest of the VCSELS are turned on, and the opposite or wholly different combination of VCSELS may be turned on or off preferably row by row and column by column (although a more sophisticated system may permit individual VCSELs to be turned on or off). The VCSELs may alternatively be always on, and then their light may be selectively blocked from reaching the microarray 104, e.g., using pairs of relatively rotatable polarizers or moveable or rotatable mirrors or absorption filters. As indicated, it may simply be desired to illuminate all of the sample spots at the same time by permitting all of the VCSELs to illuminate corresponding sample spots simultaneously. Advantageously, an m×n or i×j or 1×j or i×1 VCSEL array 102 illustrated at FIGS. 1 and 2 may be used to excite multiple cells of a microarray 104 simultaneously, instead of doing a one sample spot by one sample spot scan using a single laser.

In an exemplary VCSEL design process, p and n metal contacts and electronic routing lines are configured in such a way that rows or columns of VCSELs can be turned on or off selectively. For example, an n-contact of rows can be buried under a passivation layer and made accessible through vertical vias. Then, p-contacts may be deposited on top of the passivation layer so that they are directly accessible, or verse versa. Certain binary electronic circuitry can be implemented on chip monolithically or off chip through hybrid integration to enable the on and off logic.

For a microarray 104 with a pitch of spots that is smaller than that of the VCSEL array 102, certain rows or columns of the VCSEL array 102 can be turned on or off to match the pitches of both arrays and to reduce noise that may otherwise be caused by unused excitation light. For a microarray 104 with a finer pitch, the scan can be done in multiple steps with step size equal to the microarray pitch to cover the whole sample. Preferably, m×n spots can be read at one time and by repeating the m×n scans, an entire microarray 104 can be processed. Thus, the reading speed can be increased over a single spot system by m×n times.

Assays may have various spot sizes. Therefore, in accordance with another advantageous feature of a system in accordance with a preferred embodiment, a scan scheme is provided that is flexible so that the size of the illumination laser beam at the microarray 104 can be adjusted to cover the whole spot in order to achieve high signal level and better signal to noise ratio (SNR). For VCSELs, the aperture and single mode design provide a small Gaussian beam diameter of less than around 10 µm. This is advantageously about the same size as smaller beam spots on microarray chips 104. The beam size could be reduced with an aperture or lens if smaller sample spot sizes exist than the illumination spot sizes of the VCSELs being used can provide.

One of the unique properties of a Gaussian beam is that the beam increases its diameter with propagation distance but without changing either its profile or intensity distribution. FIG. 3 is a plot that illustrates how the diameter of a divergent Gaussian VCSEL beam increases with propagation distance. The distance labeled "d" in FIG. 3 is the diameter of a Gaussian beam at the beam propagation distance provided at the x axis. The diameter of the VCSEL beam increases approximately linearly with distance from 50 to 500 microns from its output aperture. In FIG. 3, the Gaussian beam has a 8 µm waist. FIGS. 4A and 4B illustrate beam profile cross sections of a VCSEL laser (8 µm waist) at 0 and 1 mm travel distance, with the Gaussian beam diameters being 8 and 60 µm at these two locations, respectively.

This feature permits the system of the preferred embodiment, which is adjustable as to the relative distance between the VCSEL array 102 and microarray 104, to accommodate sample spot sizes having various dimensions. The microlens array 106 may be relatively adjustable as to its distance from the microarry 104 and/or the detector array 108. The relative adjustability of relative distances can be provided in many ways including having multiple VCSEL subarrays located in different planes and/or by permitting all or subsets of the VCSELs to be translationally adjustable relative to the plane of the microarray 104. Utilizing this feature, for arrays with larger spot size, the laser illumination size on the microarray can be adjusted simply by increasing the distance between the laser and chip to match the diameter of the beam to that of the spot without the need of any optics.

The system of the preferred embodiment provides higher throughput by illuminating multiple sample spots simultaneously. Screening speeds are dramatically increased and the cost of the reader actually drops due to the relatively inexpensive nature of the VCSEL light sources, e.g., compared with systems utilizing gas lasers. In addition, the system permits the measurement of microarrays of various pitch and spot size. The system can be fully automated, either by manual input at a keyboard, or by using sensors to determine how to adjust the spot size and which VCSELs should be turned on or off depending on the contents of the microarray 104.

While an exemplary drawing and specific embodiments of the present invention have been described and illustrated, it is to be understood that that the scope of the present invention is not to be limited to the particular embodiments discussed. Thus, the embodiments shall be regarded as illustrative rather than restrictive, and it should be understood that variations may be made in those embodiments by workers skilled in the arts without departing from the scope of the present invention, which is provided in the appended claims along with structural and functional equivalents thereof.

In addition, in methods that may be performed according to preferred embodiments herein and that may have been described above, the operations have been described in selected typographical sequences. However, the sequences have been selected and so ordered for typographical convenience and are not intended to imply any particular order for performing the operations.

Although the invention has been described with reference to the above examples, it will be understood that modifications and variations are encompassed within the spirit and scope of the invention. Accordingly, the invention is limited only by the following claims.

What is claimed is:

1. An optical micro-array reader system, comprising: (a) a microchip array including multiple sample spots to be separately analyzed; (b) a vertical cavity surface emitting laser (VCSEL) array including multiple VCSELs disposed to simultaneously illuminate more than one of the multiple spots; (c) a detector array for receiving optical emissions from the sample spots; and (d) a microlens array for focusing the optical emission from the sample spots onto elements of the detector array, wherein the microlens array is located between the VCSEL and the detector array 2. The system of claim 1, wherein the VCSEL array is adjustably disposed at a selected distance from the microchip array so that an illumination spot size is provided at the microchip array that depends on the distance and which is selected based on sample spot size.

3. The system of claim 2, further comprising a filter of the VCSEL light disposed between the microchip array and the detector.

4. The system of claim 2, wherein the VCSEL array comprises m rows and n columns of VCSELs, and is configured such that one or more entire rows or one or more entire columns, or both, may be selectively energized simultaneously to illuminate said multiple sample spots.

5. The system of claim 4, wherein a first subset of VCSELs is disposed at a first distance from the microchip array so that the illumination spot sizes have a first dimension, and a second subset of VCSELs is disposed at a second distance from the microchip array so that the illumination spot sizes have a second dimension different from the first, and wherein one of the first and second rows is selectively energized depending on the sample spot size being illuminated.

6. The system of claim 1, wherein a first subset of VCSELs is disposed at a first distance from the microchip array so that the illumination spot sizes have a first dimension, and a second subset of VCSELs is disposed at a second distance from the microchip array so that the illumination spot sizes have a second dimension different from the first, and wherein one of the first and second rows is selectively energized depending on the sample spot size being illuminated.

7. The system of claim 6, wherein the VCSEL array is also adjustably disposed at a selected distance from the microchip array for further providing an illumination spot size at the microchip array that depends on the distance and which is selected based on sample spot size.

8. The system of claim 6, further comprising a filter of the VCSEL light disposed between the microchip array and the detector.

9. The system of claim 6, wherein the VCSEL array comprises m rows and n columns of VCSELs, and is configured such that one or more entire rows or one or more entire columns, or both, may be selectively energized simultaneously to illuminate said multiple sample spots.

10. The system of claim 1, wherein the optical emissions comprise fluorescence emissions.

11. A method of operating an optical micro-array reader system that includes microchip, VCSEL, microlens and detector arrays, comprising: (a) providing the microchip array with multiple sample spots to be separately analyzed; (b) energizing the VCSEL array that includes multiple VCSELs to simultaneously illuminate more than one of the multiple spots; (c) focusing optical emissions from the sample spots onto elements of the detector array through the microlens array; and (d) detecting the focused optical emissions from the sample spots, wherein the microlens array is located between the VCSEL and the detector array 12. The method of claim 11, further comprising processing data of the detected optical emissions for analysis and storage.

13. The method of claim 11, further comprising selecting and adjusting a distance between the VCSEL array and the microchip array so that an illumination spot size is provided at the microchip array that depends on the distance and which is selected based on sample spot size.

14. The method of claim 13, further comprising filtering the VCSEL light between the microchip array and the detector.

15. The method of claim 13, wherein the VCSEL array comprises m rows and n columns of VCSELs, and the method further comprising selectively energizing one or more entire rows or one or more entire columns, or both, of the VCSEL array simultaneously to illuminate said multiple sample spots.

16. The method of claim 13, wherein a first subset of VCSELs is disposed at a first distance from the microchip array so that the illumination spot sizes have a first dimension, and a second subset of VCSELs is disposed at a second distance from the microchip array so that the illumination spot sizes have a second dimension different from the first, and the method further comprises selectively energizing one of the first and second subsets depending on the sample spot size being illuminated.

17. The method of claim 11, wherein a first subset of VCSELs is disposed at a first distance from the microchip array so that the illumination spot sizes have a first dimension, and a second subset of VCSELs is disposed at a second distance from the microchip array so that the illumination spot sizes have a second dimension different from the first, and the method further comprises selectively energizing one of the first and second subsets depending on the sample spot size being illuminated.

18. The method of claim 17, further comprising adjustably disposing the VCSEL array at a selected distance from the microchip array for further providing an illumination spot size at the microchip array that depends on the distance and which is selected based on sample spot size.

19. The method of claim 17, further comprising filtering the VCSEL light between the microchip array and the detector.

20. The method of claim 17, wherein the VCSEL array comprises m rows and n columns of VCSELs, and is configured such that one or more entire rows or one or more entire columns, or both, and the method comprises selectively energizing one or more of the columns or rows, or both, simultaneously to illuminate said multiple sample spots.

21. The method of claim 11, wherein the optical emissions comprise fluorescence emissions.

22. One or more processor readable storage devices having processor readable code embodied thereon, said processor readable code for programming one or more processors to perform a method of operating an optical micro-array reader system that includes microchip, VCSEL, microlens and detector arrays, the method comprising: (a) providing the microchip array with multiple sample spots to be separately analyzed; (b) energizing the VCSEL away that includes multiple VCSELs to simultaneously illuminate more than one of the multiple spots; (c) focusing optical emissions from the sample spots onto the detector array through the microlens array; and (d) detecting the focused optical emissions, wherein the microlens array is located between the VCSEL and the detector array.

23. The one or more storage devices of claim 22, the method further comprising processing data of the detected fluorescence emissions for analysis and storage 24. The one or more storage devices of claim 22, the method further comprising selecting and adjusting a distance between the VCSEL array and the microchip array so that an illumination spot size is provided at the microchip array that depends on the distance and which is selected based on sample spot size.

25. The one or more storage devices of claim 24, the method further comprising filtering the VCSEL light between the microchip array and the detector.

26. The one or more storage devices of claim 24, wherein the VCSEL array comprises m rows and n columns of VCSELs, and the method further comprises selectively energizing one or more entire rows or one or more entire columns, or both, of the VCSEL array simultaneously to illuminate said multiple sample spots.

27. The one or more storage devices of claim 24, wherein a first subset of VCSELs is disposed at a first distance from the microchip array so that the illumination spot sizes have a first dimension, and a second subset of VCSELs is disposed at a second distance from the microchip array so that the illumination spot sizes have a second dimension different from the first, and the method further comprises selectively energizing one of the first and second subsets depending on the sample spot size being illuminated.

28. The one or more storage devices of claim 22, wherein a first subset of VCSELs is disposed at a first distance from the microchip array so that the illumination spot sizes have a first dimension, and a second subset of VCSELs is disposed at a second distance from the microchip array so that the illumination spot sizes have a second dimension different from the first, and the method further comprises selectively energizing one of the first and second subsets depending on the sample spot size being illuminated.

29. The one or more storage devices of claim 28, the method further comprising adjustably disposing the VCSEL array at a selected distance from the microchip array for further providing an illumination spot size at the microchip array that depends on the distance and which is selected based on sample spot size.

30. The one or more storage devices of claim 28, the method further comprising filtering the VCSEL light between the microchip array and the detector.

31. The one or more storage devices of claim 28, wherein the VCSEL array comprises m rows and n columns of VCSELs, and is configured such that one or more entire rows or one or more entire columns, or both, and the method comprises selectively energizing one or more of the columns or rows, or both, simultaneously to illuminate said multiple sample spots.

32. The one or more storage devices of claim 22, wherein the optical emissions comprise fluorescence emissions.

* * * * *

UNITED STATES PATENT AND TRADEMARK OFFICE
CERTIFICATE OF CORRECTION

| | | |
|---|---|---|
| PATENT NO. | : 7,453,916 B2 | Page 1 of 1 |
| APPLICATION NO. | : 11/222992 | |
| DATED | : November 18, 2008 | |
| INVENTOR(S) | : Roulin Li et al. | |

It is certified that error appears in the above-identified patent and that said Letters Patent is hereby corrected as shown below:

In column 6, line 14, in Claim 1, after "array" insert -- . --.

In column 7, line 2, in Claim 11, after "array" insert -- . --.

In column 7, line 61, in Claim 22, delete "away" and insert -- array --, therefor.

In column 8, line 9, in Claim 23, after "storage" insert -- . --.

Signed and Sealed this

Twenty-seventh Day of January, 2009

JOHN DOLL
*Acting Director of the United States Patent and Trademark Office*